US00PP28389P3

(12) United States Plant Patent
Jones

(10) Patent No.: US PP28,389 P3
(45) Date of Patent: Sep. 12, 2017

(54) ***AGASTACHE* PLANT NAMED 'AADPE14-1'**

(50) Latin Name: *Agastache mexicana*
Varietal Denomination: AADPE14-1

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 135 days.

(21) Appl. No.: 14/545,915

(22) Filed: Jul. 6, 2015

(65) Prior Publication Data

US 2017/0013765 P1 Jan. 12, 2017

(51) Int. Cl.
*A01H 5/02* (2006.01)

(52) U.S. Cl.
USPC ..... Plt./399

(58) Field of Classification Search
USPC ..... Plt./263.1, 399
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Agastache* cultivar named 'AADPE14-1' is disclosed, characterized by peach flowers and terminal bracts, uniform inflorescence and very compact plant form. The new variety is a *Agastache*, normally produced as an outdoor garden or container plant.

2 Drawing Sheets

Figure 1:
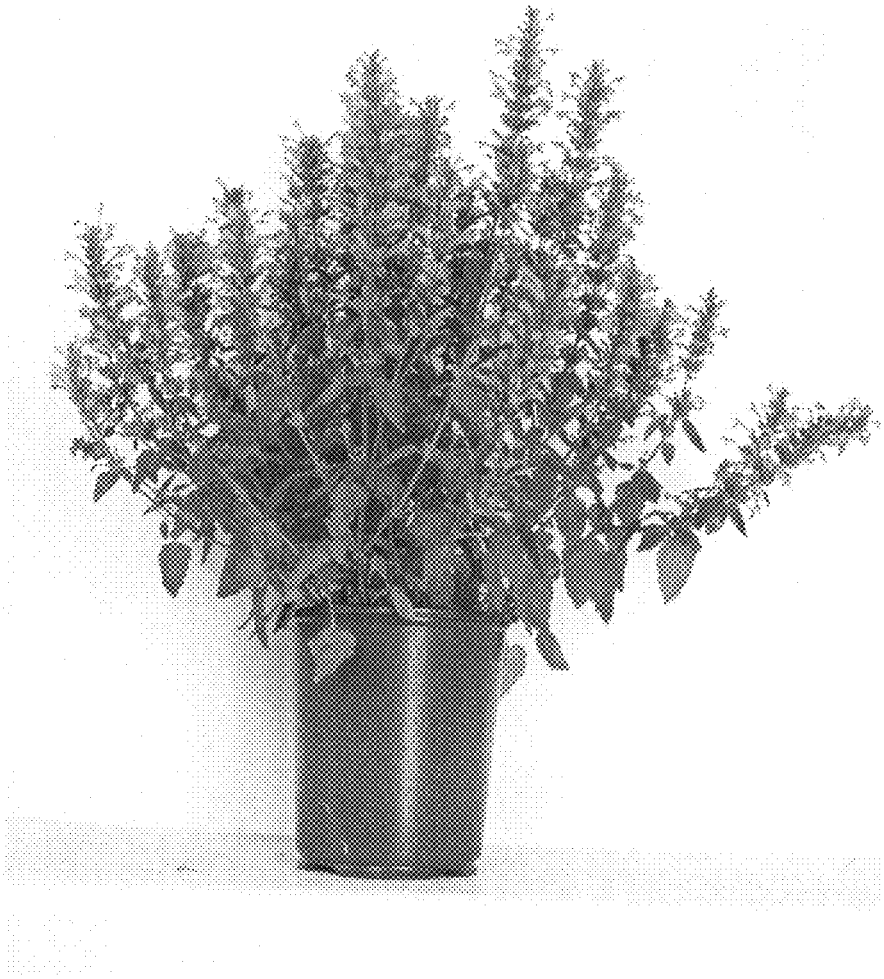

Latin name of the genus and species: *Agastache mexicana.*

Variety denomination: 'AADPE14-1'.

BACKGROUND OF THE INVENTION

The new *Agastache* cultivar is a product of a planned breeding program conducted by the inventor, Steve Jones, at a commercial greenhouse in Santa Paula, Calif. The objective of the breeding program was to produce new *Agastache* varieties for ornamental commercial applications. Selection of this new variety was made during Spring of 2012.

The parent varieties are unknown. This breeding program involved open pollination of a variety of *Agastache mexicana* varieties. Seed from the open pollination was collected in bulk, without recordation of the parent varieties. The open pollination resulting in this new variety was made during 2011.

Asexual reproduction of the new cultivar was performed by vegetative terminal cuttings. This was first performed at a research greenhouse in Santa Paula, Calif. in Spring of 2012 and has shown that the unique features of this cultivar are stable and reproduced true to type in multiple successive generations.

SUMMARY OF THE INVENTION

The cultivar 'AADPE14-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AADPE14-1' These characteristics in combination distinguish 'AADPE14-1' as a new and distinct *Agastache* cultivar:

1. Unique peach flower color.
2. Upright plant habit.

3. Highly floriferous plants.
4. Strong plants resist bending under the weight of flowers.

COMMERCIAL COMPARISON

Plants of the new cultivar 'AADPE14-1' are comparable to the unpatented commercial variety *Agastache* Acapulco 'White Yellow'. The two *Agastache* varieties are similar in most horticultural characteristics; however, the new variety 'AADPE14-1' differs in the following:

1. Flowers of the new variety are held in a more upright habit.
2. Plants of the variety are more compact in habit.
3. Plants of the new variety produce more flowers per plant.
4. Flowers of the new variety rebloom more consistently.
5. Flowers of the new variety Yellow-Orange, Orange and Red-Orange. Flowers of this comparator are Yellow and White.

Plants of the new cultivar 'AADPE14-1' can also be comparable to the unpatented commercial variety *Agastache* Acapulco 'Red'. The two *Agastache* varieties are similar in most horticultural characteristics; however, the new variety 'AADPE14-1' differs in the following:

1. Plants of the new variety are stronger and more upright, with flower stalks not bending under the weight of the flowers.
2. Plant habit of the new variety is more compact than that of this comparator.
3. The new variety is easier to propagate than this comparator.
4. Flowers of the new variety Yellow-Orange, Orange and Red-Orange. Flowers of this comparator are Red.

BRIEF DESCRIPTION OF THE PHOTOGRAPHS

The accompanying photograph in FIG. 1 illustrates in full color a typical plant of 'AADPE14-1' grown outdoors, in a 1 gallon pot. Age of the plant photographed is approximately 20 weeks from a rooted cutting.

Figure 2:
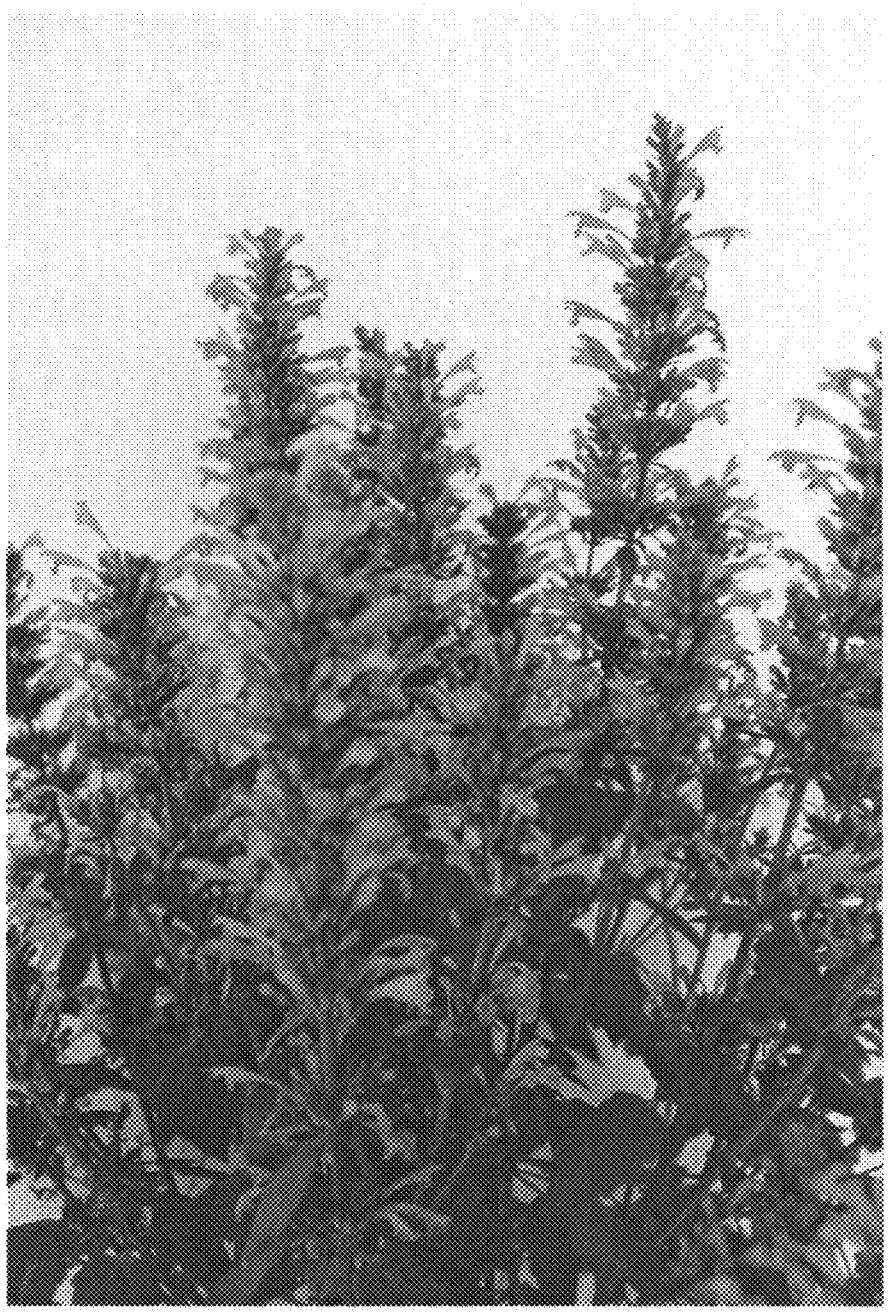

FIG. 2 illustrates a close up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'AADPE14-1' plants grown from approximately mid December until mid April, in a greenhouse, in Santa Paula, Calif. The growing temperature ranged from 20° C. to 30° C. during the day and from 15° C. to 25° C. during the night. General light conditions are bright, normal sunlight. Measurements and numerical values represent averages of typical plant types.

Botanical classification: *Agastache* 'AADPE14-1'.

PROPAGATION

Time to initiate roots: About 20 days at approximately 20 to 22° C.

Root description: Fine, densely fibrous.

Time to produce a rooted cutting: About 21 days at 22° C.

PLANT

Growth habit: Upright annual.

Pot size of plant described: 2 gallon.

Height: Approximately 30 cm to top of flowering plane, approximately 21 cm to top of foliage plane.

Plant spread: Approximately 50 cm.

Growth rate: Rapid.

Branching characteristics: Free-branching.

Length of primary lateral branches: Approximately 14 cm, foliage section only.

Diameter of lateral branches: Approximately 0.3 cm.

Quantity of lateral branches: Approximately 4 to 8 branches emerge from a pinch.

Stem:

- *Color*.—Near RHS Yellow-Green 144C.
- *Pubescence*.—Short, dense pubescence.
- *Other stem characteristics*.—Quadrangular.

Internode length: Averages between 2.5 to 5.0 cm.

Age of plant described: Approximately 20 weeks from 3 rooted cuttings.

FOLIAGE

Leaf:

- *Arrangement*.—Opposite.
- *Quantity*.—Approximately 6 to 10 fully expanded leaves per main branch.
- *Average length*.—Approximately 4.0 cm.
- *Average width*.—Approximately 2.5 cm.
- *Shape of blade*.—Deltoid.
- *Apex*.—Acute.
- *Base*.—Cordate.
- *Attachment*.—Stalked.
- *Margin*.—Crenate.
- *Texture of top surface*.—Short, dense pubescence.
- *Texture of bottom surface*.—Slightly pubescent.
- *Color*.—Young foliage upper side: Near RHS Green 137A. Young foliage under side: Near RHS Green 138B. Mature foliage upper side: Near RHS Green 137A. Mature foliage under side: Near RHS Green N138B.
- *Venation*.—Type: Pinnate. Venation color upper side: Near RHS Yellow-Green 144A. Venation color under side: Near RHS Green 138C.
- *Petiole*.—Average Length: Approximately 1.1 cm. Diameter: Approximately 1.2 cm. Color: Near Green 137B.

FLOWER

Natural flowering season: Flowering begins early Spring and continues through late Summer.

Inflorescence type and habit: Flowers arranged in verticillasters on spikes. Individual flowers self-cleaning, calyx persistent.

Flower longevity on plant: Individual flowers approximately 8 days on the plant without significant color loss or other degradation.

Quantity of flowers: Between 15 and 30 fully opened flowers per blooming spike, at one time; about 50 blooming spikes per plant.

Inflorescence size:

- *Diameter*.—Approximately 8.0 cm.
- *Height*.—Approximately 12.0 cm.

Peduncle:

- *Length*.—Average 2.5 cm.
- *Diameter*.—0.1 cm.
- *Color*.—Near RHS Green 138A.
- *Orientation*.—Straight.
- *Strength*.—Strong.

Corolla:

- *Petal arrangement*.—The corolla is highly fused, zygomorphic, bilabiate. 1 upper lip with 2 lobes, and 2 smaller lateral petals with single lobes and 2 slightly larger highly fused lobes forming a lower lip.
- *Margin*.—Entire.
- *Petal apex shape*.—Obtuse.
- *Length*.—Upper lip Approximately 0.5 cm, lower lip Approximately 0.7 cm. Laterals Approximately 0.3 cm.
- *Width*.—Upper lip Approximately 0.5 cm, lower lip Approximately 0.8 cm, Laterals Approximately 0.3 cm.
- *Entire corolla length*.—Approximately 3.1 cm.
- *Entire corolla width*.—Approximately 0.9 cm.
- *Texture*.—Glabrous.
- *Aspect*.—75° to 90° to stem.
- *Persistence*.—Non-persistent.
- *Fragrance*.—Very aromatic.

Color: Petals.

- *When opening*.—Interior surface: Near RHS Yellow-Orange 22A. Exterior surface: Near RHS Yellow-Orange 23B.
- *Fully opened*.—Interior surface: Near RHS Orange 29D. Exterior surface: Near RHS Orange 29B and Orange 29A, both colors present individually.
- *Fading*.—Interior surface: Near RHS Orange-Red 31D. Exterior surface: Near RHS Orange-Red 31C.

Floral tube:

- *When opening*.—Interior surface: Near RHS Yellow 4C. Exterior surface: Near RHS Yellow 3C.

*Fully opened*.—Interior surface: Near RHS Orange 29C. Exterior surface: Near RHS Orange 26C.

*Fading*.—Interior surface: Near RHS Red 47B. Exterior surface: Near RHS Orange 27C at base, upper tube near Orange-Red 31C.

Bud:

*Shape*.—Ovoid.

*Length*.—Approximately 1.0 cm.

*Diameter*.—Approximately 0.2 cm.

1. *Color*.—Near RHS Orange 26B.

Calyx:

*Length*.—Approximately 0.7 cm.

*Diameter*.—Approximately 0.2 cm.

*Shape*.—Tubular.

Sepals:

*Shape*.—5 sepals fused to form a tube.

*Apex*.—Highly acute.

*Margin*.—Entire.

*Texture*.—Pubescent.

*Color*.—Near RHS 137C, very faintly flushed RHS Greyed-Purple 183A.

*Persistence*.—Persistent.

REPRODUCTIVE ORGANS

Stamens:

*Number*.—4.

*Filament length*.—Approximately 2.1 cm lower 50% to 75% fused to petals.

Anthers:

*Shape*.—Elliptic.

*Length*.—Approximately 1 mm.

*Color*.—Near RHS Greyed-Purple N186A.

*Pollen*.—Scant.

*Pollen color*.—Near RHS Yellow-White 158D.

Pistil:

*Number*.—1.

*Length*.—Approximately 3.0 cm, not fused to floral parts.

*Style*.—Length: Approximately 2.9 cm. Color: Near RHS Yellow-White 158D.

*Stigma*.—Shape: Linear, or occasionally very small two-parted cleft. Color: Near RHS Greyed-Red 181C. Ovary color: Near RHS Yellow-White 158A.

OTHER CHARACTERISTICS

Seeds and fruits: Seed and fruit production has not been observed.

Disease/pest resistance: Neither resistance nor susceptibility observed. *Agastache* is Typical diseases include *Pythium* and *Phytopthera*. Various species of White Fly, Aphis and Mites may infect *Agastache*.

Temperature tolerance: Perennial to USDA zone 5.

What is claimed is:

1. A new and distinct cultivar of *Agastache* plant named 'AADPE14-1' as herein illustrated and described.

* * * * *